United States Patent
Furuya et al.

(10) Patent No.: US 10,343,951 B2
(45) Date of Patent: *Jul. 9, 2019

(54) MAGNESIUM FLUORIDE SINTERED COMPACT, METHOD FOR MANUFACTURING MAGNESIUM FLUORIDE SINTERED COMPACT, NEUTRON MODERATOR, AND METHOD FOR MANUFACTURING NEUTRON MODERATOR

(71) Applicants: NIPPON LIGHT METAL COMPANY, LTD., Tokyo (JP); Cancer Intelligence Care Systems, Inc., Tokyo (JP); SINTER LAND Incorporation, Ltd., Niigata (JP)

(72) Inventors: Hidaka Furuya, Aichi (JP); Yoshinori Sugawara, Tokyo (JP); Hideaki Usui, Tokyo (JP); Kazuto Sanada, Tokyo (JP); Masaru Nakamura, Tokyo (JP); Shinichi Takei, Niigata (JP)

(73) Assignees: NIPPON LIGHT METAL COMPANY, LTD., Tokyo (JP); Cancer Intelligence Care Systems, Inc., Tokyo (JP); SINTER LAND Incorporation, Ltd., Niigata (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/874,496

(22) Filed: Jan. 18, 2018

(65) Prior Publication Data

US 2018/0141869 A1 May 24, 2018

Related U.S. Application Data

(63) Continuation of application No. PCT/JP2016/071263, filed on Jul. 20, 2016.

(30) Foreign Application Priority Data

Jul. 21, 2015 (JP) ................................ 2015-144389

(51) Int. Cl.
*C04B 35/553* (2006.01)
*C04B 35/645* (2006.01)
(Continued)

(52) U.S. Cl.
CPC .......... *C04B 35/553* (2013.01); *A61K 41/009* (2013.01); *A61N 5/10* (2013.01);
(Continued)

(58) Field of Classification Search
CPC .......... A61K 41/009; A61K 5/10; H05H 3/06; A61N 2005/109; C04B 2235/105;
(Continued)

(56) References Cited

U.S. PATENT DOCUMENTS 3,301,781 A   1/1967   Rice et al.
5,880,478 A   3/1999   Bishop et al.
(Continued)

FOREIGN PATENT DOCUMENTS

AU   2015210075   8/2016
CN   1763239 A    4/2006
(Continued)

OTHER PUBLICATIONS

Notification of Reason for Refusal dated Nov. 20, 2017 in Korean Application No. 10-2016-7019974; English Translation.
(Continued)

*Primary Examiner* — Nicole M Ippolito
(74) *Attorney, Agent, or Firm* — Rankin, Hill & Clark LLP

(57) ABSTRACT

According to an aspect, a magnesium fluoride sintered compact includes a disc-shaped magnesium fluoride sintered
(Continued)

compact having a through hole passing through a center axis of the disc-shaped magnesium fluoride sintered compact. The magnesium fluoride sintered compact has a relative density of 95% or higher.

15 Claims, 15 Drawing Sheets

(51) Int. Cl.
    *C04B 37/00*     (2006.01)
    *A61K 41/00*     (2006.01)
    *A61N 5/10*     (2006.01)
    *H05H 3/06*     (2006.01)
    *B32B 18/00*     (2006.01)

(52) U.S. Cl.
    CPC ............ *B32B 18/00* (2013.01); *C04B 35/645* (2013.01); *C04B 37/001* (2013.01); *H05H 3/06* (2013.01); *A61N 2005/109* (2013.01); *C04B 2235/445* (2013.01); *C04B 2235/6021* (2013.01); *C04B 2235/6028* (2013.01); *C04B 2235/6562* (2013.01); *C04B 2235/6567* (2013.01); *C04B 2235/666* (2013.01); *C04B 2235/72* (2013.01); *C04B 2235/94* (2013.01); *C04B 2235/95* (2013.01); *C04B 2237/36* (2013.01); *C04B 2237/62* (2013.01)

(58) Field of Classification Search
    CPC ...... C04B 2235/445; C04B 2235/6021; C04B 2235/6028; C04B 2235/666; C04B 2237/36; C04B 2237/62; C04B 35/553; C04B 35/645; C04B 37/001
    USPC ................................. 250/505.1, 515.1, 517.1
    See application file for complete search history.

(56) References Cited

U.S. PATENT DOCUMENTS

| | | | |
|---|---|---|---|
| 9,868,673 B2* | 1/2018 | Furuya | A61N 5/10 |
| 2003/0112916 A1 | 6/2003 | Keeney | |
| 2008/0175936 A1 | 7/2008 | Tokita et al. | |
| 2010/0025594 A1 | 2/2010 | Nukatsuka et al. | |
| 2010/0248935 A1 | 9/2010 | Teratani et al. | |
| 2012/0211284 A1 | 8/2012 | Digiovanni | |
| 2013/0087499 A1 | 4/2013 | Uda | |
| 2013/0163711 A1 | 6/2013 | Zabiego et al. | |
| 2013/0294563 A1 | 11/2013 | Nagata et al. | |
| 2016/0002116 A1* | 1/2016 | Kumada | C04B 35/6261 423/497 |
| 2016/0020839 A1 | 1/2016 | Kim et al. | |
| 2016/0082282 A1 | 3/2016 | Kumada | |

FOREIGN PATENT DOCUMENTS

| | | |
|---|---|---|
| CN | 101068640 | 11/2007 |
| CN | 103026419 | 4/2013 |
| CN | 104575653 A | 4/2015 |
| EP | 1895819 A1 | 3/2008 |
| EP | 3098209 A1 | 11/2016 |
| JP | 07216409 A | 8/1995 |
| JP | 11139862 A | 5/1999 |
| JP | 11228248 A | 8/1999 |
| JP | 200086344 A | 3/2000 |
| JP | 2003049207 A | 2/2003 |
| JP | 2004507713 | 3/2004 |
| JP | 2004233168 A | 8/2004 |
| JP | 200896405 A | 4/2008 |
| JP | 2008230904 A | 10/2008 |
| JP | 2009192488 A | 8/2009 |
| JP | 2012206913 A | 10/2012 |
| JP | 201362193 A | 4/2013 |
| JP | 2013217874 A | 10/2013 |
| JP | 2015052540 A | 3/2015 |
| KR | 10-2013-0031340 | 3/2013 |
| RU | 2436877 C1 | 12/2011 |
| TW | 201502073 A | 1/2015 |
| UA | 12384 A | 2/1997 |
| WO | 2014010704 A1 | 1/2014 |
| WO | 2015005006 A1 | 1/2015 |

OTHER PUBLICATIONS

Tatli, Zafer et al., "SPS sintering of silicon nitride with fluoride additive," Ceramics International, 2014, pp. 1399-1404, vol. 40, Elsevier, The Netherlands.

International Search Report dated Sep. 13, 2016 filed in PCT/JP2016/071263.

Khorsandi, B. et al., "Optimizing the OSU-ABNS Base Moderator Assembly Materials for BNCT", 2004, a Nuclear Engineering Program, The Ohio State University, Columbus, OH USA; Cited in Specification.

Kononov, O.E. et al., "Accelerator-Based source of epithermal neutrons for neutron capture therapy", 2004, pp. 626-631, vol. 97 No. 3, Atomic Energy, Springer Science Business Media, Inc. Germany; Cited in Specification.

Third Party Observation to International Application No. PCT/JP2016/071263 dated Aug. 10, 2017.

Nakamura, Masaru, et al., "Reappraisal of the optimal neutron energy characteristic and spectrum for accelerator based epithermal neutron source-PHITS analysis and trial production of the moderator", Sep. 12, 2012, 15th International congress of Neutron Capture Therapy; Cited in Third Party Observation of International App. PCT/JP2016/071263; English Translation.

Fy Heisei 24, "Development of Accelerator Type Neutron Capture Therapy System Using New Material Target Technology for Recurrent Cancer Therapy" Feb. 2013; Cited in Third Party Observation of International Application No. PCT/JP2016/071263; Englsih Translation.

Fy Heisei 25, "Development of Accelerator Type Neutron Capture Therapy System Using New Material Target Technology for Recurrent Cancer Therapy", Feb. 2014; Cited in Third Party Observation of International Application No. PCT/JP2016/071263; English Translation.

FY 2014 (Heisei 26), "Development of Accelerator Type Neutron Capture Therapy System Using New Material Target Technology for Recurrent Cancer Therapy", Feb. 2015; Cited in Third Party Observation of International Application No. PCT/JP2016/071263; English Translation.

Office Action of Taiwanese Application No. 105123042 dated Apr. 25, 2017.

International Search Report of International Application No. PCT/JP2015/051419 dated Apr. 21, 2015; Submitted reference in U.S. Appl. No. 15/216,536.

Inoue, R. et al., "Optimum design of a moderator system based on dose calculation for an accelerator driven Boron Neutron Capture Therapy", Applied Radiation and Isotopes 83, 2014, pp. 225-228, Elsevier Ltd., UK; Submitted reference in U.S. Appl. No. 15/216,536.

Kononov, O.E. et al., "Optimization of an accelerator-based epithermal neutron source for neutron capture therapy", Applied Radiation and Isotopes 61, 2014, pp. 1009-1013, Elsevier Ltd., UK; Submitted reference in U.S. Appl. No. 15/216,536.

Notice of Allowance dated Aug. 15, 2017 filed in U.S. Appl. No. 15/216,536.

Shirakawa, Youichi, et al., "Preparation of $MgF_2$ Sintered Body by Normal Sintering Combined with Capsule-Free Hot-Isostatic Pressing Treatment", Journal of the Ceramic Society of Japan, 1999, pp. 1137-1139, vol. 107 No. 12; Submitted reference in U.S. Appl. No. 15/216,536.

Extended European Search Report of European application No. 15740248.8 dated Aug. 30, 2017; Submitted reference is U.S. Appl. No. 15/216,536.

Notice of Reasons for Revocation of a Patent of Japanese patent No. 6085782B1 dated Nov. 13, 2017; Submitted reference in U.S. Appl. No. 15/216,536; English Translation.

(56) References Cited

OTHER PUBLICATIONS

Tokita, Masao, "Recent and Future Progress on Advanced Ceramics Sintering by Spark Plasma Sintering (SPS) Method", Ceramis, 2014, pp. 91-96, vol. 49 No. 2; Submitted reference in U.S. Appl. No. 15/216,536; English Translation.
Written Opposition to the grant of a Patent of Japanese patent No. 6085782B1 dated Jun. 6, 2017; Submitted reference in U.S. Appl. No. 15/216,536; English Translation.
Office Action of Russian application No. 2016133616 dated Oct. 23, 2017; Submitted reference in U.S. Appl. No. 15/216,536; English Translation.
Poddenezhnyi, E.N. et al., "Ceramic Fluoride Targets for Magnetron Sputtering Formed by a Method of Semidry Compaction with Vacuum Sealing", "VESTNIK of GSTU named after P.O.Sukhoi", 2012, pp. 62-67, No. 3; Submitted reference in U.S. Appl. No. 15/216,536; English abstract.
Chinese Office Action dated Oct. 15, 2018 issued in the corresponding Chinese patent application No. 201580005534.6 and its English translation.
Korean Office Action (KROA) dated May 18, 2018 issued in the corresponding Korean patent application No. 10-2018-7001855 and its English translation.
Office Action dated Feb. 22, 2019 issued in the corresponding Australian patent application No. 2016294873.
Extended European Search Report (EESR) dated Feb. 19, 2019 issued in the corresponding European patent application No. 16827790.3.

* cited by examiner

MAGNESIUM FLUORIDE SINTERED COMPACT, METHOD FOR MANUFACTURING MAGNESIUM FLUORIDE SINTERED COMPACT, NEUTRON MODERATOR, AND METHOD FOR MANUFACTURING NEUTRON MODERATOR

CROSS-REFERENCE TO RELATED APPLICATIONS

This application is a continuation of International Application No. PCT/JP2016/071263, filed on Jul. 20, 2016, which claims priority to Japanese Application No. 2015-144389, filed on Jul. 21, 2015. The contents of these applications are incorporated herein by reference in their entirety.

BACKGROUND

1. Technical Field

The present disclosure relates to a neutron moderator mainly used for neutron capture therapy, a method for manufacturing the neutron moderator, a magnesium fluoride sintered compact that is optimal for a neutron moderator, and a method for manufacturing the magnesium fluoride sintered compact.

2. Description of the Related Art

Various materials have been studied for a neutron moderator that is used for selective treatment of cancer such as boron neutron capture therapy. Examples of the materials include lithium fluoride, aluminum fluoride, and magnesium fluoride. Of these materials, magnesium fluoride is specifically known as an optimal material for a neutron moderator due to its excellent function in moderating the energy of neutron beams to 10 keV or lower.

The technique described in Japanese Patent Application Laid-open No. 2004-233168 (JP-A-2004-233168) uses lithium fluoride for a neutron moderator. Lithium used in the technique described in JP-A-2004-233168, however, presents an issue of manufacturing cost, because Lithium is one of rare metals.

In view of the above issue, "Optimizing the OSU-ABNS Base Moderator Assembly Materials for BNCT B. Khorsandia*, T. E. Blue a Nuclear Engineering Program, The Ohio State University, Columbus, Ohio 43210, USA" describes that magnesium fluoride has an excellent neutron moderating function for moderating the energy of neutrons in the range of 10 keV or lower. In addition, "Accelerator-Based source of epithermal neutrons for neutron capture therapy. Kononov O E, Kononov V N, Solov' EV A N, Bokhovko M V At Energy Vol. 97 No. 3, PP 626-631" describes a moderator combining magnesium fluoride and polytetrafluoroethylene.

In order to manufacture a neutron moderator only with magnesium fluoride and without using polytetrafluoroethylene to have a good neutron moderating performance, it is appropriate to process magnesium fluoride into a sintered compact. For a neutron moderator, a magnesium fluoride sintered compact is preferably made into a predetermined volume, to be free from cracks and chipping, and to have a high relative density.

The present disclosure has been made in view of the above considerations, and is directed to providing a magnesium fluoride sintered compact to be free from cracks and chipping and to have a high relative density, a method for manufacturing the magnesium fluoride sintered compact, a neutron moderator, and a method for manufacturing the neutron moderator.

SUMMARY

According to an aspect of the present disclosure in order to solve the above-mentioned problems and achieve the purpose, a magnesium fluoride sintered compact of the present disclosure is provided. The magnesium fluoride sintered compact includes a disc-shaped magnesium fluoride sintered compact having a through hole passing through a center axis of the disc-shaped magnesium fluoride sintered compact. The magnesium fluoride sintered compact has a relative density of 95% or higher.

This configuration provides a magnesium fluoride sintered compact less prone to damages such as cracking due to machining.

According to a preferred aspect of the present disclosure, it is preferable that the through hole has a tapered inner wall with a diameter gradually changing along the center axis. This configuration enables insertion of a target.

According to a preferred aspect of the present disclosure, a neutron moderator preferably includes: a plurality of the magnesium fluoride sintered compacts; and a plurality of disc-shaped magnesium fluoride sintered compacts without a through hole. The magnesium fluoride sintered compacts and the magnesium fluoride sintered compacts without a through hole are combined and layered. The neutron moderator can suppress neutrons having energy of lower than 0.5 eV by including the magnesium fluoride sintered compact that is free from cracks and chipping and that has a high relative density. The neutron moderator can also suppress neutrons having energy of higher than 10 keV by including the magnesium fluoride sintered compact that is free from cracks and chipping and that has a high relative density.

According to a preferred aspect of the present disclosure, it is preferable that at least one of the disc-shaped magnesium fluoride sintered compacts without a through hole has a tapered outer peripheral surface. This configuration can reduce the amount of machining for the outer periphery shape.

In order to solve the above-mentioned problems and achieve the purpose, a method for manufacturing a magnesium fluoride sintered compact of the present disclosure is provided. The method includes: filling a magnesium fluoride powder material into a sintering die by tapping, the sintering die being provided with a core at a center position in a planar view; and performing pulsed electric current sintering for sintering the filled magnesium fluoride powder material while applying mechanical pressure and a direct current with a waveform of an ON-OFF pulse voltage thereto, to obtain a magnesium fluoride sintered compact having a through hole at a center thereof. The core has a coefficient of thermal expansion equivalent to a coefficient of thermal expansion of the magnesium fluoride sintered compact.

This manufacturing method can provide a magnesium fluoride sintered compact to be free from cracks and chipping and to have a high relative density.

According to a preferred aspect of the present disclosure, it is preferable that the core is made of a nickel-based alloy. This configuration provides a magnesium fluoride sintered compact that is free from cracks and chipping and that is capable of withstanding the sintering temperature for magnesium fluoride.

According to a preferred aspect of the present disclosure, it is preferable that in the powder filling, the magnesium fluoride powder material is a high-purity material having a purity of 99 percent by mass or higher, the balance being inevitable impurities. The magnesium fluoride sintered compact made of such a high-purity material can suppress neutrons having energy of lower than 0.5 eV. The magnesium fluoride sintered compact can also suppress neutrons having energy of higher than 10 keV.

According to a preferred aspect of the present disclosure, a method for manufacturing a neutron moderator preferably includes: preparing a plurality of magnesium fluoride sintered compacts, each having the through hole at the center and being manufactured by the method for manufacturing a magnesium fluoride sintered compact; machining the magnesium fluoride sintered compacts each having the through hole at the center; and layering and joining together the magnesium fluoride machined bodies each having the through hole after the machining and a plurality of disc-shaped magnesium fluoride sintered compacts in combination. The neutron moderator can suppress neutrons having energy of lower than 0.5 eV by including the magnesium fluoride sintered compact that is free from cracks and chipping and that has a high relative density. The neutron moderator can also suppress neutrons having energy of higher than 10 keV by including the magnesium fluoride sintered compact that is free from cracks and chipping and that has a high relative density.

According to a preferred aspect of the present disclosure, it is preferable that the machining includes tapering the through hole at the center for the magnesium fluoride sintered compacts each having the through hole at the center. This configuration can reduce the amount of boring.

According to a preferred aspect of the present disclosure, it is preferable that the disc-shaped magnesium fluoride sintered compacts each have a tapered outer peripheral shape. This configuration can increase the precision of the outer peripheral shape.

According to a preferred aspect of the present disclosure, it is preferable that sintered molded bodies each having a tapered outer peripheral shape are obtained as the disc-shaped magnesium fluoride sintered compacts. This configuration can reduce the amount of machining for the outer peripheral shape.

The present disclosure can provide a magnesium fluoride sintered compact to be free from cracks and chipping and to have a high relative density, a method for manufacturing the magnesium fluoride sintered compact, a neutron moderator, and a method for manufacturing the neutron moderator.

DETAILED DESCRIPTION

The following describes modes (embodiments) for carrying out the present disclosure in detail with reference to the accompanied drawings. The description in the following embodiment is not intended to limit the present disclosure. Components described below include those that can easily be conceived by those skilled in the art and that are substantially the same. Furthermore, the components described below can be combined as appropriate.

Neutron Source Generator

Figure 1:
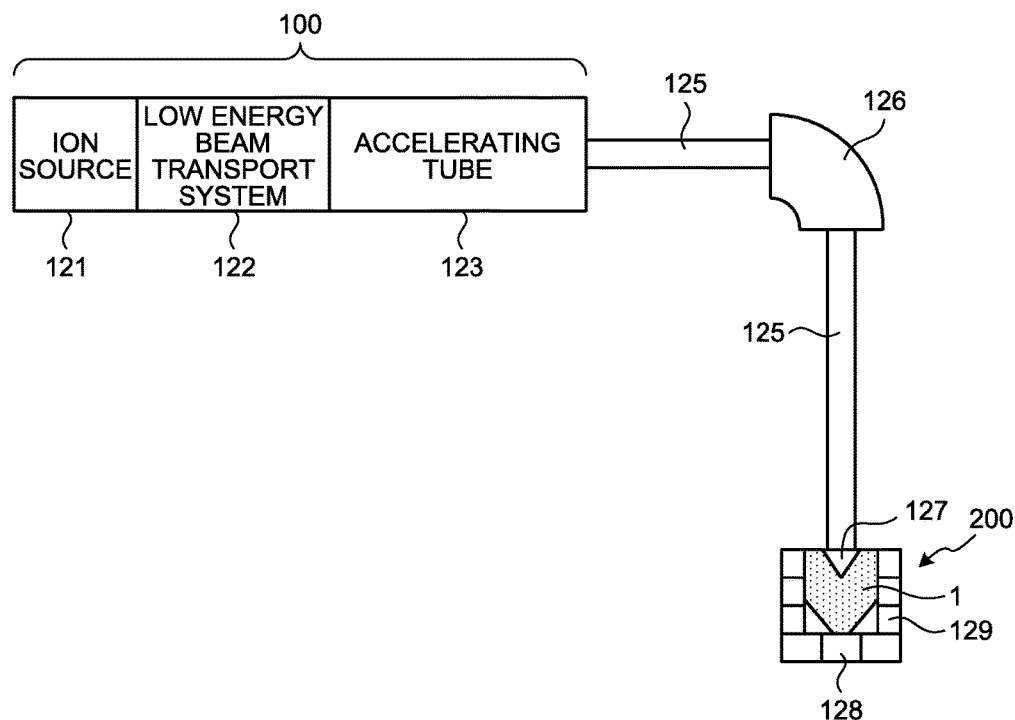
FIG. 1 is a diagram for explaining a neutron source generator including a neutron moderator according to an embodiment.

FIG. 1 is a diagram for explaining a neutron source generator including a neutron moderator according to an embodiment. As illustrated in FIG. 1, the neutron source generator includes an accelerator 100, a beam transport 125, a bending magnet 126, and a target unit 200.

The accelerator 100 is a device for accelerating protons and is provided with an ion source 121, a low energy beam transport system (LEBT) 122, and an accelerating tube 123 in this order from upstream to downstream. The ion source 121 is a device for turning protons into cations. The low energy beam transport system 122 is an interface between the ion source 121 and the accelerating tube 123.

The beam transport 125 is a beam passage for guiding protons accelerated by the accelerator 100 to the target unit 200. The beam transport 125 changes the traveling direction of the accelerated protons through the bending magnet 126 so that the protons are guided to the target unit 200 disposed in an optional position. In this manner, the bending magnet 126 is used to bend the traveling direction of the protons accelerated by the accelerator 100. The beam transport 125 may guide the protons accelerated by the accelerator 100 to the target unit 200 without using the bending magnet 126.

The target unit 200 is a device for generating neutrons by a reaction of protons and a target 127. The target unit 200 includes the target 127, a neutron moderator 1, a neutron reflector 129, and an irradiation part 128.

The target 127 includes a base (substrate), such as of copper, on which a target material, such as a thin film of metallic lithium, is deposited. The target 127 described in the embodiment is a cone-shaped target with a lithium thin film provided on its inner wall surface (inner surface). The target material is not limited to this shape. A target of any shape, for example, a plate-shaped target with a lithium thin film provided on its surface, may be used. The target material may be another target material such as beryllium. The neutron moderator 1 moderates neutrons generated by the target 127.

The neutron reflector 129 is made of lead, for example, and surrounds the target 127 and the neutron moderator 1 to prevent unnecessary release of neutrons to the outside of the target unit 200. The irradiation part 128 is an opening for releasing the neutrons moderated by the neutron moderator 1.

Neutron capture therapy, which selectively kills cancer cells, has been studied recently and clinically tested in nuclear facilities. The neutron source generator illustrated in FIG. 1 can provide neutrons without use of a nuclear reactor. In neutron capture therapy, medicine is prepared from a chemical compound containing a substance, such as non-radioactive isotope boron-10 (B-10) that easily causes nuclear reaction with thermal neutrons, for example. The medicine is preliminarily administered to a human so that the medicine is absorbed in an area where cancer exists, i.e., only in cancer cells coexisting with normal cells. Neutron capture therapy is cancer therapy to selectively suppress only cancer cells by irradiating, by the neutron source generator illustrated in FIG. 1, a cancer site with neutrons (thermal neutrons and epithermal neutrons) of an energy that has less influence on a human body.

The neutron moderator 1 needs to moderate the energy of the released neutrons to the range of 10 keV or lower so that the neutrons (thermal neutrons and epithermal neutrons) have an energy that has less influence on a human body. The neutron moderator 1 of the embodiment is made of magnesium fluoride and moderates neutrons, and thus presents high neutron moderating performance in the energy range of 20 keV or lower.

Effective neutron energy used as radiation for treating recurrent cancer is generally from 0.5 eV to 10 keV. Neutron energy of lower than 0.5 eV is likely to affect normal tissues in a skin surface of a human body, while neutron energy of higher than 10 keV has a larger effect on normal tissues other than cancer tissues inside a human body. Compared with a heavy water moderator, the neutron moderator 1 of the embodiment can suppress more neutrons having energy of lower than 0.5 eV than the heavy water moderator does. Compared with a polytetrafluoroethylene moderator, the neutron moderator 1 of the embodiment can suppress more neutrons having energy of higher than 10 keV than the polytetrafluoroethylene moderator does.

In order for the neutron moderator 1 of the embodiment made of magnesium fluoride to have a predetermined passage cross-sectional area, it is preferable that magnesium fluoride be formed into a sintered compact. However, if a magnesium fluoride sintered compact has enough size as the neutron moderator 1 of the embodiment, it has been found that a magnesium fluoride sintered compact needs some technique to maintain the quality of its sintered state, such as prevention of cracking or chipping. The following describes the neutron moderator 1 in detail with reference to FIG. 2 to FIG. 17.

Neutron Moderator

Figure 2:
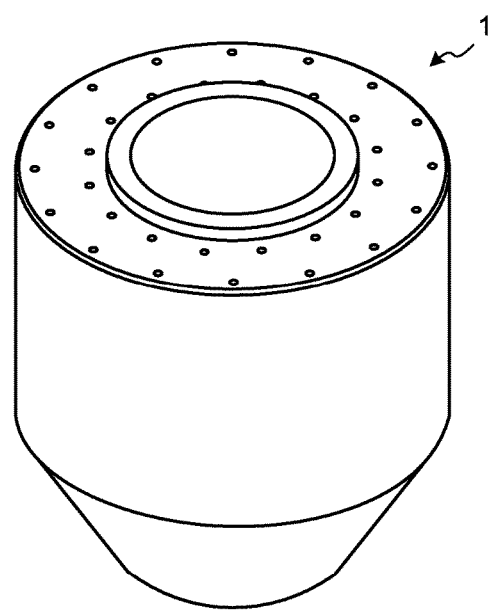
FIG. 2 is a perspective view of the neutron moderator according to the embodiment.
Figure 3:
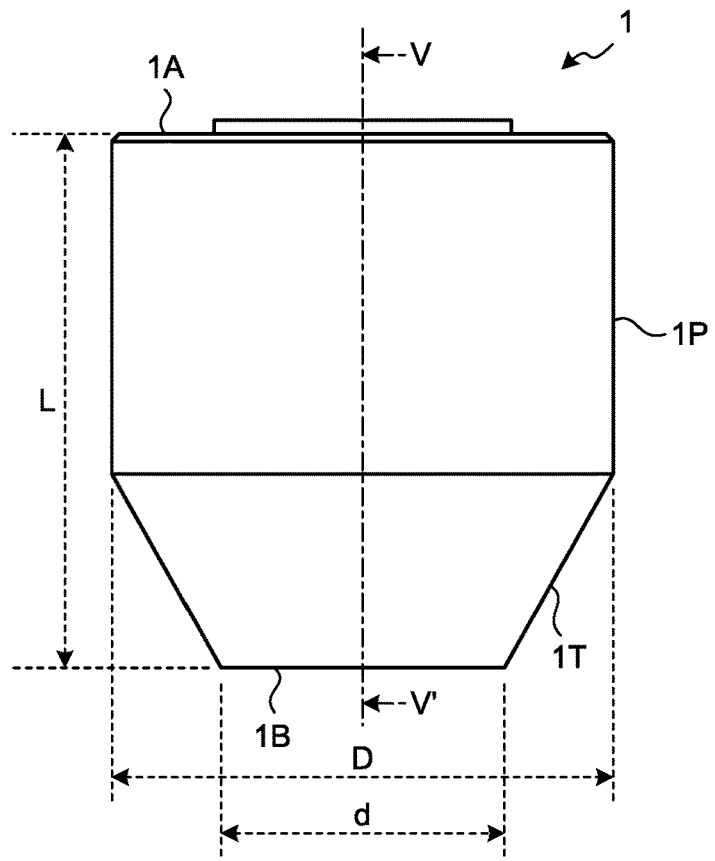
FIG. 3 is a side view of the neutron moderator in FIG. 2.
Figure 4:
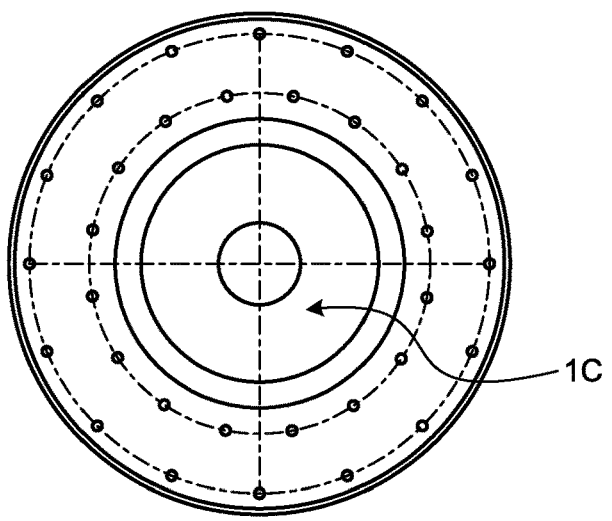
FIG. 4 is a top view of the neutron moderator in FIG. 2.
Figure 5:
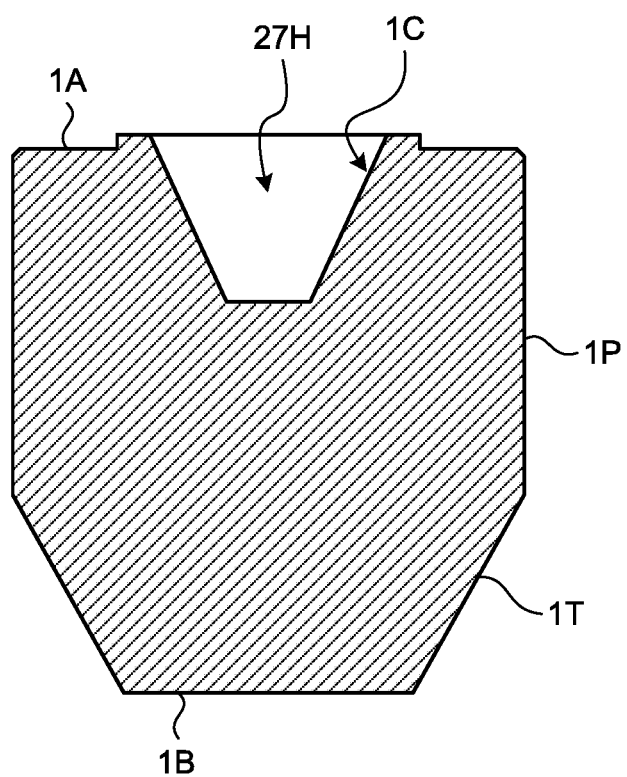
FIG. 5 is a sectional view taken along V-V' in FIG. 3.

FIG. 2 is a perspective view of the neutron moderator according to the embodiment. FIG. 3 is a side view of the neutron moderator in FIG. 2. FIG. 4 is a top view of the neutron moderator in FIG. 3. FIG. 5 is a sectional view taken along line V-V' in FIG. 3. The neutron moderator 1, as illustrated in FIG. 3, is a substantially cylindrical body having a top surface 1A on the target 127 side illustrated in FIG. 1, a bottom surface 1B on the irradiation part 128 side illustrated in FIG. 1, and an outer periphery 1P. As illustrated in FIG. 3, assuming that the thickness of the neutron moderator 1 is a thickness L in the travelling direction of neutrons from the target 127 to the irradiation part 128 illustrated in FIG. 1, the neutral moderator 1 tends to have a ratio of the thickness L to a diameter D (thickness L/diameter D) being 180% or higher.

When the neutron moderator 1 having such an overall shape is sintered as one piece and the neutron moderator 1 is shaped in a regular hexahedron such as a rectangular parallelepiped, many machining processes are required after sintering for shaving the neutron moderator 1 shaped in the rectangular parallelepiped, and partial cracking or chipping may render the entire neutron moderator 1 useless.

When the overall shape of the neutron moderator 1 is sintered as one piece, the partial shape of the neutron moderator 1 affects pressurization, and the inside of the neutron moderator 1 may have a lower relative density due to non-uniform pressurization.

The non-uniform relative density of the neutron moderator 1 may affect the moderation of neutrons. The neutron moderator 1 may develop cracks or chips on its outer periphery portion when the size of the neutron moderator 1 is large (specifically, with a diameter ($\phi$) of 150 mm or larger).

As illustrated in FIG. 4 and FIG. 5, the top surface 1A of the neutron moderator 1 has a tapered surface 1C of a depressed part 27H into which the target 127 illustrated in FIG. 1 is inserted. As illustrated in FIG. 3, the neutron moderator 1 has an outer peripheral tapered surface 1T, the diameter of which decreases toward the bottom surface 1B so that a diameter d of the bottom surface 1B is smaller than the diameter D of the outer periphery 1P. If the tapered surface 1C and the tapered surface 1T have large areas, it is difficult to manufacture the neutron moderator 1 with a high precision shape.

In light of the above, the inventors have arrived at a method of performing sintering by a near net shape technique with reduced machining processes in which a magnesium fluoride powder material is filled into a die installed with a core at the center. Specifically, when performing sintering, the core is provided at the center of the sintering die to yield a ring-shaped magnesium fluoride sintered compact. This reduces the processes and time for drilling after sintering, which can reduce the machining cost. In addition, this can reduce cracking of a sintered compact due to machining, thereby increasing yields.

Figure 6:
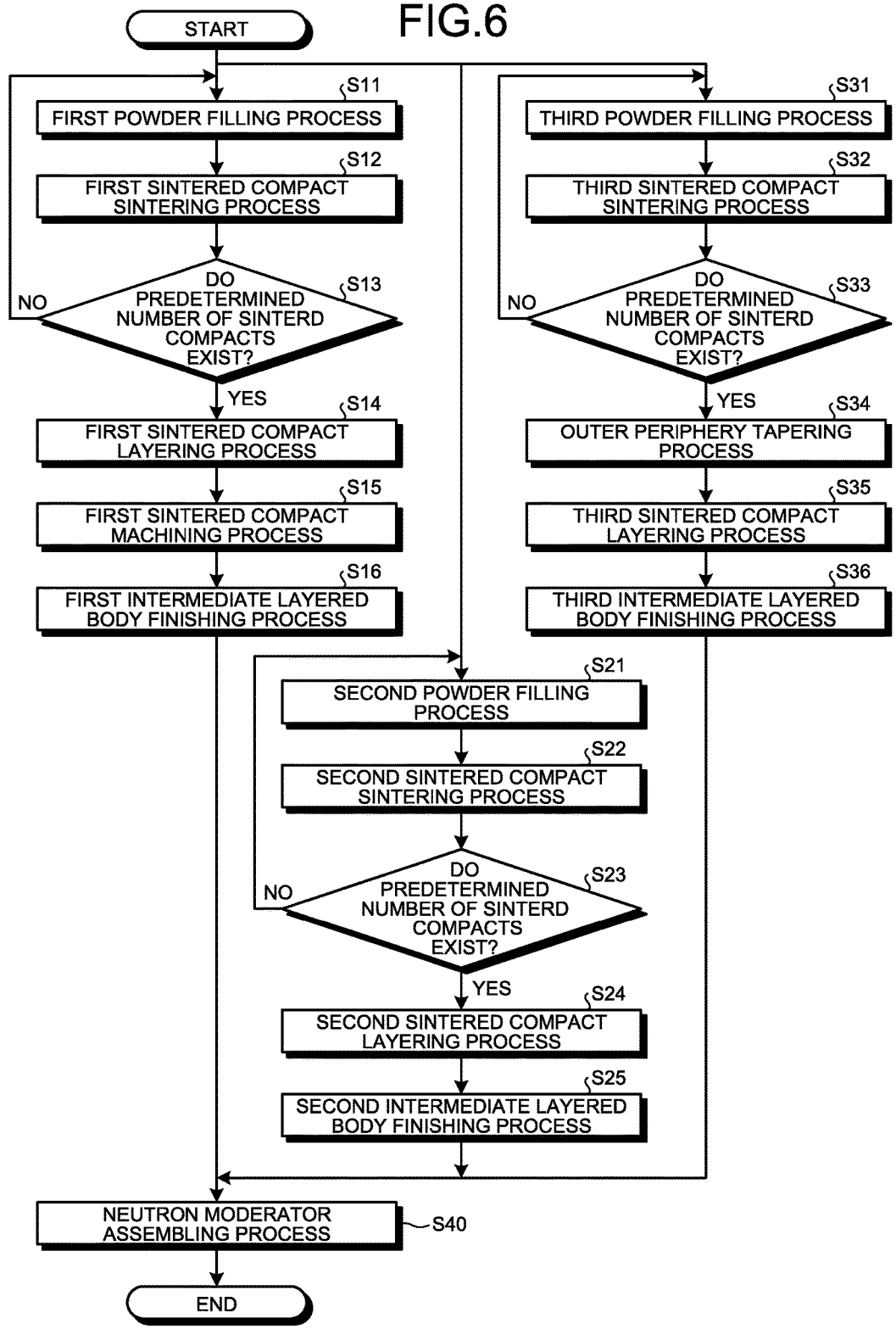
FIG. 6 is a flowchart for explaining a method for manufacturing the neutron moderator according to the embodiment.

FIG. 6 is a flowchart for explaining a method for manufacturing the neutron moderator according to the embodiment. In the method for manufacturing the sintered compact according to the embodiment, a first intermediate layered body, a second intermediate layered body, and a third intermediate layered body which are obtained through the processes of manufacturing the first intermediate layered body, the second intermediate layered body, and the third intermediate layered body, respectively, are assembled into the neutron moderator.

Process for Manufacturing First Intermediate Layered Body

Figure 7:
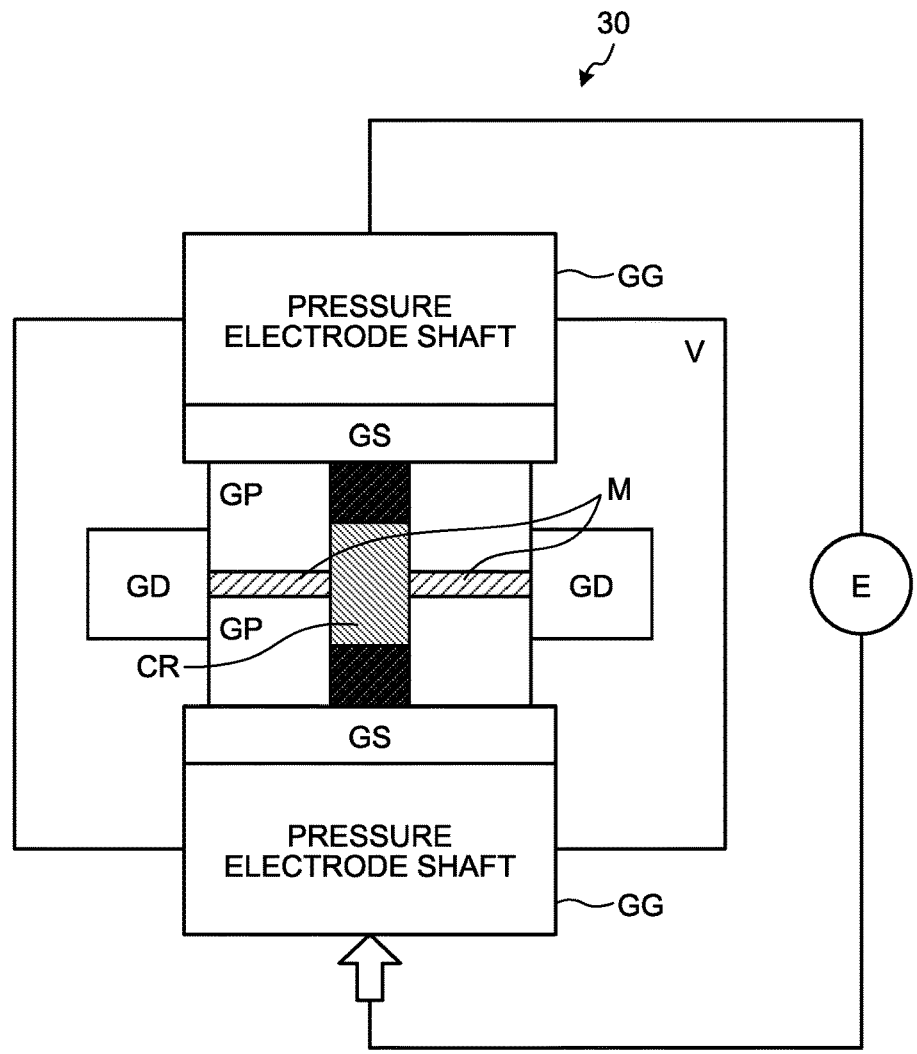
FIG. 7 is a diagram schematically illustrating a pulsed electric current sintering device for manufacturing a first sintered compact.
Figure 8:
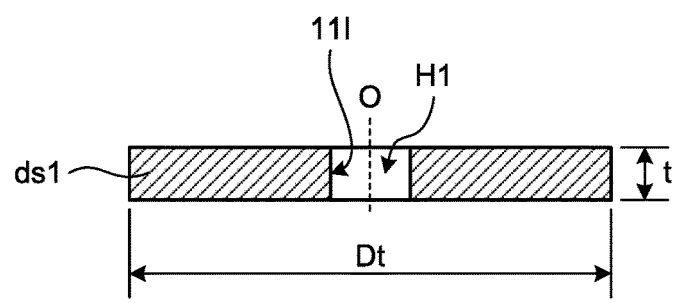
FIG. 8 a side view of the first sintered compact according to the embodiment.
Figure 9:
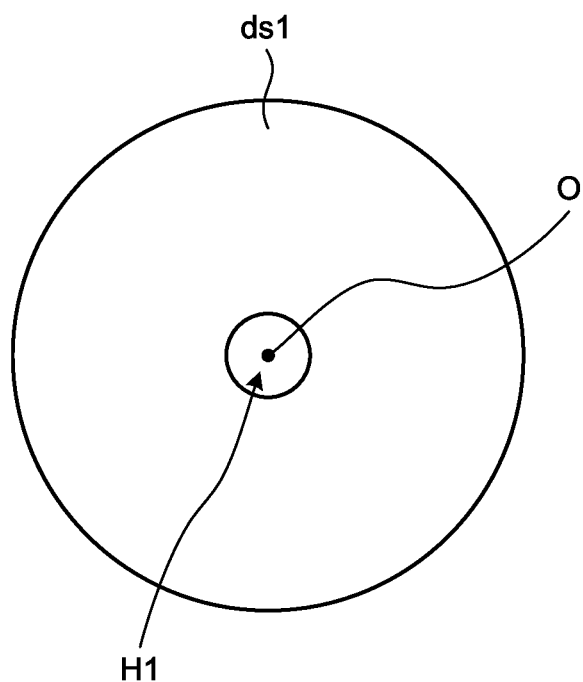
FIG. 9 is a top view of the first sintered compact in FIG. 8.
Figure 10:
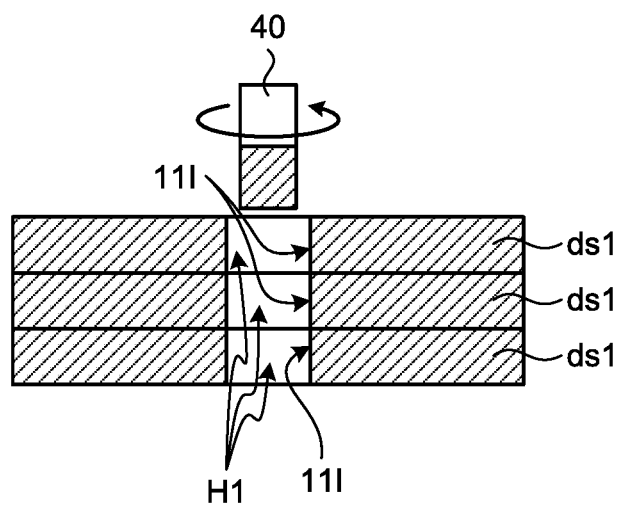
FIG. 10 is a diagram for explaining a layered state of a first intermediate layered body that is a layered body of the first sintered compacts according to the embodiment.
Figure 11:
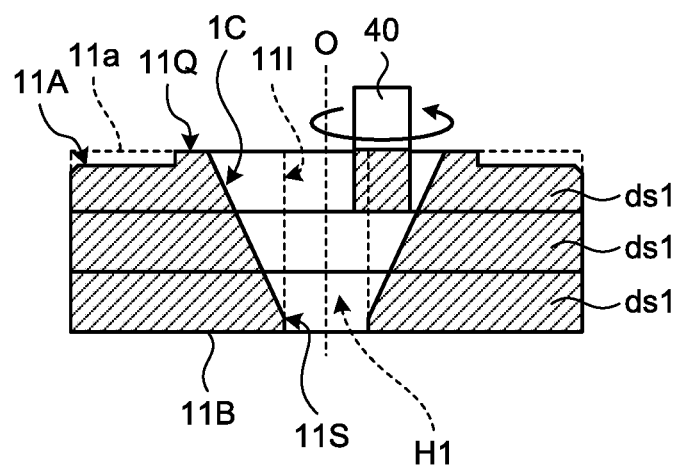
FIG. 11 is a diagram for explaining a machining process for manufacturing the first intermediate layered body according to the embodiment.
Figure 12:
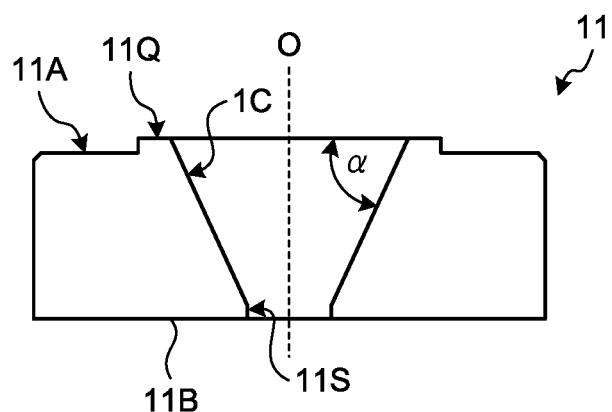
FIG. 12 is a diagram illustrating the first intermediate layered body according to the embodiment.

The process for manufacturing the first intermediate layered body will be described below with reference to FIG. 6 to FIG. 10 and, if necessary, FIG. 2 to FIG. 5. FIG. 7 is a diagram schematically illustrating a pulsed electric current sintering device for manufacturing a first sintered compact. FIG. 8 is a side view of the first sintered compact according to the embodiment. FIG. 9 is a top view of the first sintered compact in FIG. 8. FIG. 10 is a diagram for explaining a layered state of the first intermediate layered body that is a layered body of the first sintered compacts according to the embodiment. FIG. 11 is a diagram for explaining a machining process for manufacturing the first intermediate layered body according to the embodiment. FIG. 12 is a diagram illustrating the first intermediate layered body according to the embodiment.

In the method for manufacturing the magnesium fluoride sintered compact according to the embodiment, a solid compression sintering method called spark plasma sintering (SPS) or pulsed electric current sintering is applied to obtain the magnesium fluoride sintered compact with fewer cracks and with high yields.

In order to obtain a first intermediate layered body 11 according to the embodiment illustrated in FIG. 12, the present embodiment includes a first powder filling process S11, a first sintered compact sintering process S12, a first sintered compact layering process S14, a first sintered compact machining process S15, and a first intermediate layered body finishing process S16.

As illustrated in FIG. 7, a pulsed electric current sintering device 30 includes a chamber V the inside atmosphere of which can be vacuum or purged with argon or nitrogen gas, a graphite die GD, graphite punches GP, graphite spacers GS, pressure electrode shafts GG, and a direct current pulse power source E. The graphite die GD, the graphite punches GP, the graphite spacers GS, and the pressure electrode shafts GG are made of a conductive material such as graphite and stainless steel.

The direct current pulse power source E can apply a direct current with the waveform of an ON-OFF pulse voltage to a magnesium fluoride powder material M in the graphite die GD through the graphite die GD, the graphite punches GP, and the pressure electrode shafts GG.

In the method for manufacturing the sintered compact according to the embodiment, at the first powder filling process S11, the magnesium fluoride powder material M is prepared and filled by tapping. A sintering die surrounded by the graphite die GD and the graphite punches GP forms a cylindrical hollow space. In the inside of the sintering die, a core CR is disposed at the center position in a planer view. The pulsed electric current sintering device 30 applies pressure between the two pressure electrode shafts GG to compact the filled powder with the core CR being held.

The core CR according to the embodiment is a cylinder having a predetermined diameter. Here, a coefficient of thermal expansion of magnesium fluoride is $8.48 \times 10^{-6}/°$ C. to $13.7 \times 10^{-6}/°$ C. A coefficient of thermal expansion of the core CR is equivalent to that of the magnesium fluoride sintered compact. Being equivalent to the coefficient of thermal expansion of the magnesium fluoride sintered compact means that the coefficient of thermal expansion of the material of the core CR is in the range of $8.48 \times 10^{-6}/°$ C. to $13.7 \times 10^{-6}/°$ C. It is preferable that the material of the core CR has a melting point higher than the heating maximum temperature and the (sintering) holding temperature of magnesium fluoride. With such a material, the shape of the sintering die is maintained with the core CR serving as a sintering tool.

By employing the core CR made of the material having the coefficient of thermal expansion equivalent to that of the magnesium fluoride sintered compact, a contraction coefficient of the magnesium fluoride becomes equivalent to that of the core during cooling after sintering, thereby alleviating stress during cooling. This can lower the possibility of cracking of the sintered compact.

For example, a nickel (Ni)-based alloy is a material that has a coefficient of thermal expansion equivalent to that of magnesium fluoride and that of the magnesium fluoride sintered compact, and is capable of withstanding the sintering temperature for magnesium fluoride. The nickel (Ni)-based alloy is thus suitable as the material of the core CR. Here, the nickel (Ni)-based alloy refers to an alloy containing 50 or more percent by mass of nickel (Ni).

To be more specific, the material of the core CR is, for example, a Ni-based NiFeCr alloy that contains 10 percent by mass to 20 percent by mass of chromium (Cr) and 5 percent by mass to 10 percent by mass of Fe, and the balance being Ni. The NiFeCr alloy has a coefficient of thermal expansion of $13.5 \times 10^{-6}/°$ C., for example, and a melting point of 1400° C. to 1500° C. The NiFeCr alloy contains inevitable impurities.

The material of the core CR may be, for example, an FeCr alloy that is a ferrite-based Fe alloy containing 11 percent by mass to 15 percent by mass of chromium (Cr) and the balance being Fe (for example, JIS SUS405). The FeCr alloy (for example, JIS SUS405) has a coefficient of thermal expansion of, for example, $10 \times 10^{-6}/°$ C. to $13.5 \times 10^{-6}/°$ C. and a melting point of 1500° C. The ferrite-based FeCr alloy contains inevitable impurities.

In the method for manufacturing the sintered compact according to the embodiment, at the first sintered compact sintering process S12, mechanical pressure and a direct current with the waveform of an ON-OFF pulse voltage are applied to sinter the magnesium fluoride powder material M (pulsed electric current sintering). Here, the magnesium fluoride powder material M in the graphite die GD is compressed into a ring shape with the pressure applied by the graphite punches GP and the pressure electrode shafts GG. As illustrated in FIG. 8 and FIG. 9, a first sintered compact ds1 according to the embodiment is, for example, a disc-shaped magnesium fluoride sintered compact having a thickness t and a diameter Dt and has a through hole H1 passing through the center axis O of the disc-shaped magnesium fluoride sintered compact. As illustrated in FIG. 8, an inner wall 11I has a circular shape having a predetermined diameter as viewed from above at an equal distance from the straight line passing through the center axis O. The ratio of the thickness t to the diameter Dt is more preferably 8% to 15%. This configuration can prevent the first sintered compact ds1 from cracking or chipping.

As described above, the first sintered compact ds1 is formed by filling the magnesium fluoride powder material M in the sintering die installed with the core CR for forming the through hole H1, and sintering the filled powder material. This method can reduce the number of machining processes for a depressed part 27H illustrated in FIG. 5 and reduce the possibility of damage such as cracking due to machining.

The material of the core CR has the coefficient of thermal expansion in the range from $8.48 \times 10^{-6}/°$ C. to $13.7 \times 10^{-6}/°$ C., more preferably closer to $13.7 \times 10^{-6}/°$ C. than the intermediate coefficient of thermal expansion of $8.48 \times 10^{-6}/°$ C. to $13.7 \times 10^{-6}/°$ C. While being heated and sintered at the holding temperature, the magnesium fluoride powder material M is expanded by thermal expansion, and thereafter slowly contracts during a slow cooling period. In the slow cooling period, the expanded volume of the core CR also contracts, in a similar manner. When the coefficient of thermal expansion of the material of the core CR is closer to $13.7 \times 10^{-6}/°$ C. than the intermediate coefficient of thermal expansion of $8.48 \times 10^{-6}/°$ C. to $13.7 \times 10^{-6}/°$ C., the contraction of the core CR tends to be equivalent to or faster than that of the first sintered compact ds1 in the slow cooling period. This suppresses distortion between the core CR and the inner wall 11I of the through hole H1 of the first sintered compact ds1, thereby lowering the possibility of cracking on the periphery of the inner wall 11I.

In the embodiment, when the predetermined number of first sintered compacts ds1 is three and the three first sintered compacts ds1 have yet been obtained (No at S13), the first powder filling process S11 and the first sintered compact sintering process S12 are repeated. When the predetermined number of first sintered compacts ds1 is three and the three first sintered compacts ds1 have been obtained (Yes at S13), the process proceeds to the next process (S14). Here, the predetermined number is not limited to three.

In the first sintered compact layering process S14, as illustrated in FIG. 10, the first sintered compacts ds1 are stacked, pressed. in a direction parallel to the center axis O and temporarily fixed to form the first intermediate layered body 11. The first sintered compacts ds1 are stacked such that the respective inner walls 11I of the through holes H1 are flush with one another. Adhesive may be used for the temporary fixing. The outer shape of the first intermediate layered body 11 is cylindrical.

In the embodiment, the tapered surface 1C needs to be made smooth as illustrated in FIG. 12. Subsequently, the first intermediate layered body formed at the first sintered compact layering process S14 is subjected to a first intermediate body machining process.

As illustrated in FIG. 10, at the first sintered compact machining process S15, a drill 40 which spirally revolves while rotating around its own axis is inserted into the through holes H1 of the stacked first sintered compacts ds1 to bore a tapered surface 1C illustrated in FIG. 11. As illustrated in FIG. 11, since the first sintered compacts ds1 have through holes H1 in advance, the amount of machining can be reduced compared with the case where disc-shaped sintered compacts are drilled from the beginning.

It is preferable that the angle α of the tapered surface 1C is constant among the first sintered compacts ds1 so that the tapered surface 1C is continuous at the boundary between the layered first sintered compacts ds1. The tapered surface 1C preferably has an angle according to the angle of the taper on the outer periphery of the target 127 illustrated in FIG. 1.

When the first sintered compact ds1 is machined from one surface to the other surface in order to prevent cracking or chipping, cracking or chipping tends to occur with the drill 40 being in the vicinity of the other surface. For this reason, the cutting device stops spiral revolution immediately before the drill 40 penetrates the other surface of the first sintered compact ds1, so that part of the inner wall 11I of the through hole H1 can be left as an inner wall 11S, thereby preventing cracking or chipping.

As illustrated in FIG. 11, the disc-shaped magnesium fluoride sintered compacts ds do not necessarily have the same thickness. For example, a surface 11a of one of the first sintered compacts ds1 arranged on the top may be scrapped off so that a top surface 11A is exposed while a protrusion 11Q remains around the edge of the tapered surface 1C.

When a prototype of the first intermediate layered body 11 illustrated in FIG. 12 is produced, the first sintered compacts ds1 are joined together in the thickness direction and temporarily stored at the first intermediate layered body finishing process S16.

As described above, the first sintered compact ds1 is a disc-shaped magnesium fluoride sintered compact and has the through hole H1 passing through the center axis O of the disc-shaped magnesium fluoride sintered compact. The first sintered compact ds1 is sintered such that the magnesium fluoride sintered compact obtained by sintering the magnesium fluoride powder material M has a relative density of 95% or higher. This configuration provides a magnesium fluoride sintered compact less prone to damage such as cracking due to machining. If the magnesium fluoride sintered compact has a relative density of lower than 95%, the sintering finished size increases, whereby the load on the sintering die increases and the sintering finished size increase requires more time and effort for machining. Consequently, the risk of cracking in machining may increase.

Process for Manufacturing Second Intermediate Layered Body

Figure 13:
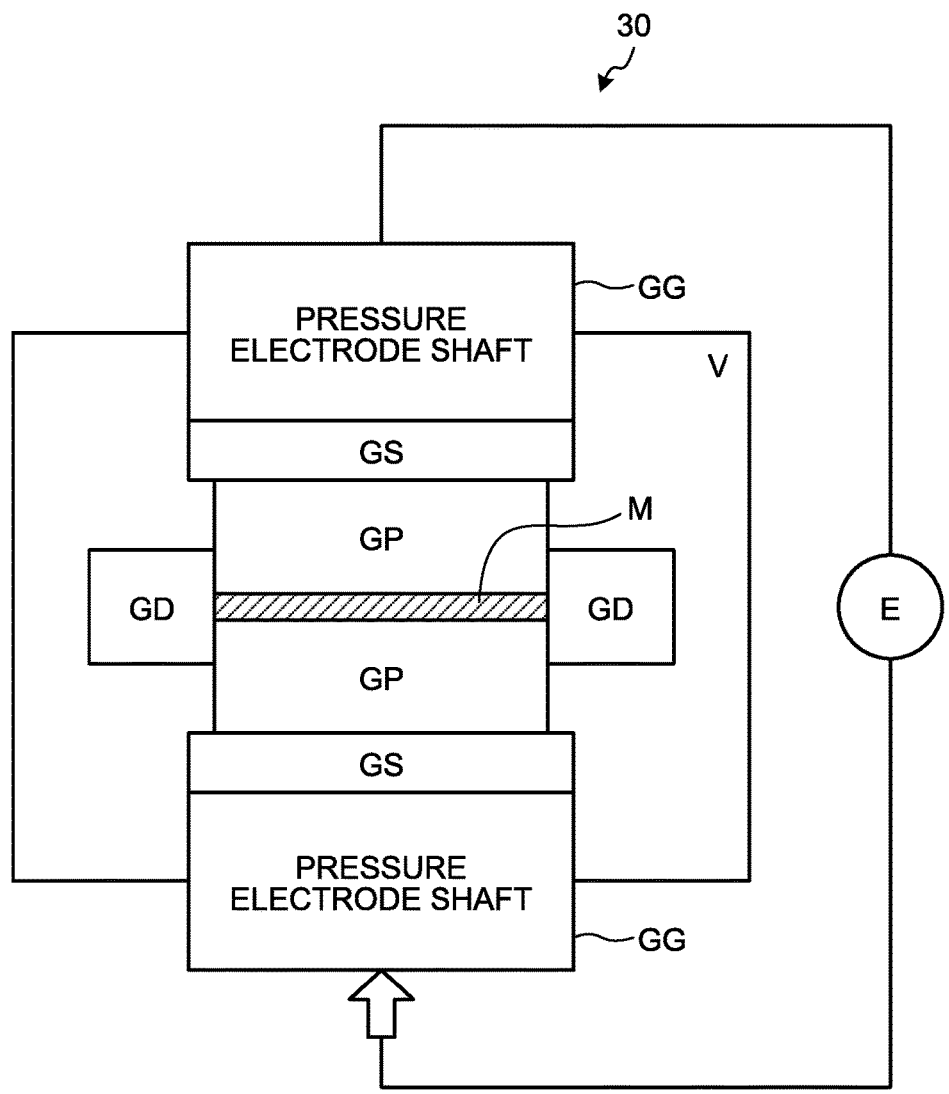
FIG. 13 is a diagram schematically illustrating a pulsed electric current sintering device for manufacturing a second sintered compact or a third sintered compact.
Figure 14:
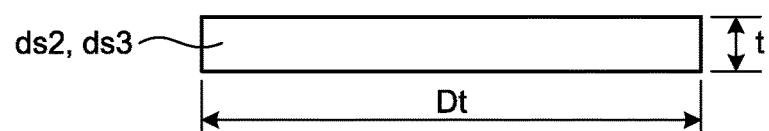
FIG. 14 is a diagram schematically illustrating a disc-shaped magnesium fluoride sintered compact.
Figure 15:
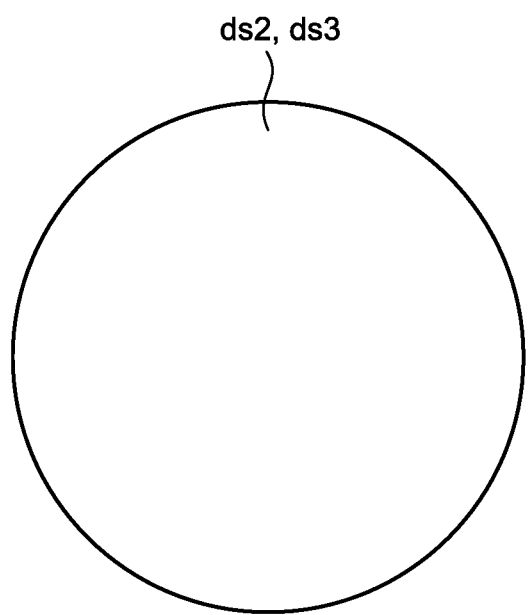
FIG. 15 is a top view of the disc-shaped magnesium fluoride sintered compact in FIG. 14.
Figure 16:
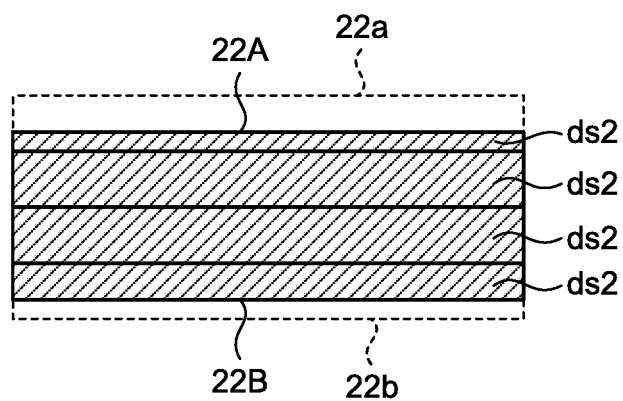
FIG. 16 is a diagram for explaining a layered state of a second intermediate layered body that is a layered body of the second sintered compacts according to the embodiment.
Figure 17:
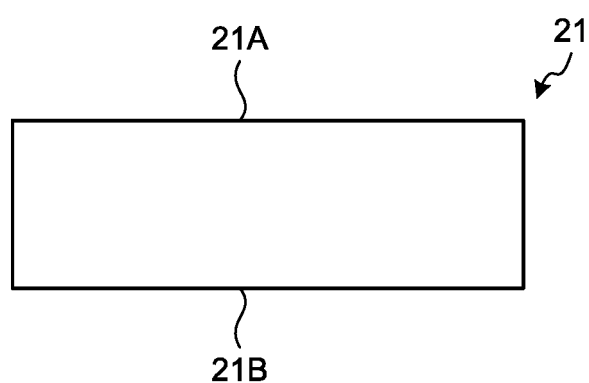
FIG. 17 is a diagram illustrating the second intermediate layered body according to the embodiment.

The process for manufacturing the second intermediate layered body will be described below with reference to FIG. 6, FIG. 13 to FIG. 17 and, if necessary, FIG. 2 to FIG. 5. FIG. 13 is a diagram schematically illustrating a pulsed electric current sintering device for manufacturing a second sintered compact or a third sintered compact. FIG. 14 is a diagram schematically illustrating a disc-shaped magnesium fluoride sintered compact. FIG. 15 is a top view of the disc-shaped magnesium fluoride sintered compact in FIG. 14. FIG. 16 is a diagram for explaining a layered state of the second intermediate layered body that is a layered body of the second sintered compacts according to the embodiment. FIG. 17 is a diagram illustrating the second intermediate layered body according to the embodiment.

In order to obtain a second intermediate layered body 21 according to the embodiment illustrated in FIG. 17, the embodiment includes a second powder filling process S21, a second sintered compact sintering process S22, a second sintered compact layering process S24, and a second intermediate layered body finishing process S25.

As illustrated in FIG. 13, a pulsed electric current sintering device 30 is similar to the above-described pulsed electric current sintering device 30 except that it does not include the core illustrated in FIG. 7. In the pulsed electric current sintering device 30 illustrated in FIG. 13, the same components as those illustrated in FIG. 7 are denoted by the same reference numerals and will not be further elaborated.

In the method for manufacturing the sintered compact according to the embodiment, at the second powder filling process S21, the magnesium fluoride powder material M is prepared and filled by tapping. A sintering die surrounded by the graphite die GD and the graphite punches GP forms a cylindrical hollow space.

In the method for manufacturing the sintered compact according to the embodiment, at the second sintered compact sintering process S22, a direct current with the waveform of an ON-OFF pulse voltage is applied to sinter the magnesium fluoride powder material M (pulsed electric current sintering). Here, the magnesium fluoride powder material N in the graphite die GD is compressed into a disc shape by pressure P applied by the graphite punches GP and the pressure electrode shafts GG. As illustrated in FIG. 14 and FIG. 15, a second sintered compact ds2 according to the embodiment is, for example, a disc-shaped magnesium fluoride sintered compact having a thickness t and a diameter Dt. The ratio of the thickness t to the diameter Dt is more preferably 8% to 15%. This configuration can prevent the third sintered compact ds3 from cracking or chipping.

In the embodiment, when the predetermined number of second sintered compacts ds2 is four and the four second sintered compacts ds2 have yet been obtained (No at S23), the second powder filling process S21 and the second sintered compact sintering process S22 are repeated. When the predetermined number of second sintered compacts ds2 is four and the four second sintered compacts ds2 have been obtained (Yes at S23), the process proceeds to the next process (S24). Here, the predetermined number is not limited to four.

Subsequently, in the method for manufacturing the neutron moderator according to the embodiment, after the disc-shaped second sintered compacts ds2 are manufactured and prepared as an intermediate layered body as described above, the second sintered compacts ds2 are layered and joined together in the thickness direction at the second intermediate layered body layering process S24.

As illustrated in FIG. 16, the disc-shaped magnesium fluoride sintered compacts ds do not necessarily have the same thickness. For example, a surface 22a of one of the disc-shaped second sintered compact ds2 arranged on the top may be scraped off so that a top surface 22A is exposed. The top surface 22A illustrated in FIG. 16 becomes a top surface 21A of the second intermediate layered body 21 illustrated in FIG. 17. A surface 22b of one of the disc-shaped second sintered compacts ds2 arranged on the bottom may be scraped off so that a bottom surface 22B is exposed. The bottom surface 22B illustrated in FIG. 16 becomes a bottom surface 21B of the second intermediate layered body 21 illustrated in FIG. 17. In the method for manufacturing the neutron moderator according to the embodiment, when a prototype of the second intermediate layered body 21 illustrated in FIG. 17 is produced at the layering process, the second intermediate layered body 21 is temporarily stored at the second intermediate layered body finishing process S25. The second intermediate layered body 21 has a cylindrical shape.

Process for Manufacturing Third Intermediate Layered Body

Figure 18:
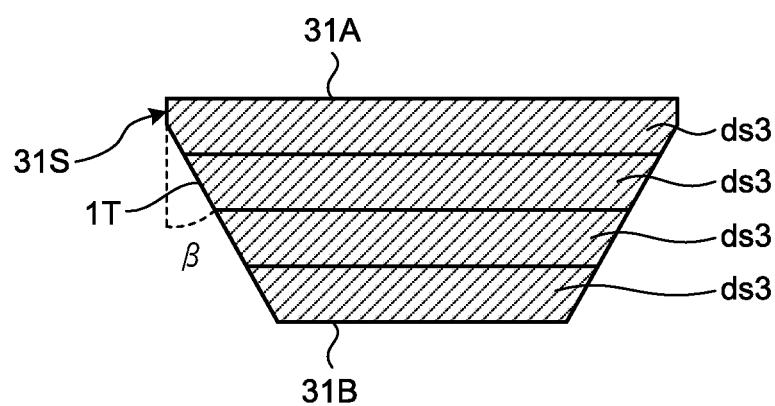
FIG. 18 is a diagram for explaining a layered state of a third intermediate layered body that is a layered body of the third sintered compacts according to the embodiment.
Figure 19:
FIG. 19 is a diagram for explaining a machining process for manufacturing the third intermediate layered body according to the embodiment.
Figure 20:
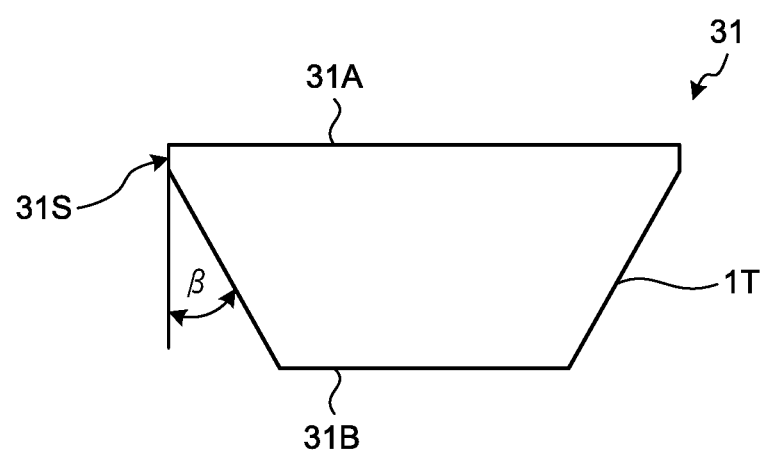
FIG. 20 is a diagram illustrating the third intermediate layered body according to the embodiment.

The process for manufacturing the third intermediate layered body will be described below with reference to FIG. 6, FIG. 13 to FIG. 15, and FIG. 18 to FIG. 20, and, if necessary, FIG. 2 to FIG. 5. FIG. 18 is a diagram for explaining a layered state of a third intermediate layered body which is a layered body of the third sintered compacts according to the embodiment. FIG. 19 is a diagram for explaining a machining process for manufacturing the third intermediate layered body according to the embodiment. FIG. 20 is a diagram illustrating the third intermediate layered body according to the embodiment.

In order to obtain a third intermediate layered body 31 according to the embodiment illustrated in FIG. 20, the embodiment includes a third powder filling process S31, a third sintered compact sintering process S32, an outer periphery tapering process S34, a third sintered compact layering process S35, and a third intermediate layered body finishing process S36.

The pulsed electric current sintering device 30 illustrated in FIG. 13 can also manufacture the third sintered compact.

In the method for manufacturing the sintered compact according to the embodiment, at the third powder filling process S31, the magnesium fluoride powder material M is prepared and filled by tapping. The sintering die surrounded by the graphite die GD and the graphite punches GP forms a cylindrical hollow space.

In the method for manufacturing the sintered compact according to the embodiment, at the third sintered compact sintering process S32, mechanical pressure and a direct current with the waveform of an ON-OFF pulse voltage are applied to sinter the magnesium fluoride powder material M (pulsed electric current sintering). Here, the magnesium fluoride powder material M in the graphite die GD is compressed into a disk shape by pressure P applied by the graphite punches GP and the pressure electrode shafts GG. As illustrated in FIG. 14 and FIG. 15, the third sintered compact ds3 according to the embodiment is, for example, a disc-shaped magnesium fluoride sintered compact having a thickness t and a diameter Dt. The ratio of the thickness t to the diameter Dt is more preferably 8% to 15%. This configuration can prevent the third sintered compact ds3 from cracking or chipping.

In the embodiment, when the predetermined number of third sintered compacts ds3 is four and the four third sintered compacts ds3 have yet been obtained (No at S33), the third powder filling process S31 and the third sintered compact sintering process S32 are repeated. When the predetermined number of third sintered compacts ds3 is four and the four third sintered compact ds3 have been obtained (Yes at S33), the process proceeds to the next process (S34). Here, the predetermined number is not limited to four.

In the embodiment, a tapered surface 1T needs to be made smooth as illustrated in FIG. 20. Here, as illustrated in FIG. 19, the outer periphery tapering process S34 is performed as machining in the embodiment. At the outer periphery tapering process S34, the drill 40 is pressed against one of the disc-shaped third sintered compacts ds3 from the outside of the outer periphery thereof to form the tapered surface 1T. A cylindrical part 31S may be left in the third sintered compact ds3 as illustrated in FIG. 18. It is preferable that the angle β of the tapered surface 1T is set to be constant considering the layering order of the disc-shaped third sintered compacts ds3.

Subsequently, after the disc-shaped third sintered compacts ds3 having the outer periphery tapered at the outer periphery tapering process S34 are prepared, the third sintered compact layering process S35 is performed considering the layering order of the disc-shaped third sintered compacts ds3 at the third sintered compact layering process S35. At the third sintered compact layering process S35, the third intermediate layered body 31 is formed by layering and joining the third sintered compacts ds3 together in the thickness direction so that the tapered surface 1T on the outer periphery is continuous in the top-bottom direction.

In the method for manufacturing the neutron moderator according to the embodiment, the third intermediate layered body 31 illustrated in FIG. 20 is manufactured as described above. The third intermediate layered body 31 has a substantially conical outer shape having a top surface 31A, a bottom surface 31B, and the tapered surface 1T. A prototype of the third intermediate layered body 31 illustrated in FIG. 20 is produced and then temporarily stored at the third intermediate layered body finishing process S36.

Neutron Moderator Assembling Process

At a neutron moderator assembling process S40, the top surface 21A of the second intermediate layered body 21 and a bottom surface 11B of the first intermediate layered body 11 are joined together. The top surface 11A of the first intermediate layered body 11 becomes the top surface 1A of the neutron moderator 1. The bottom surface 21B of the second intermediate layered body 21 and the top surface 31A of the third intermediate layered body 31 are also joined together. The bottom surface 31B of the third intermediate layered body 31 becomes the bottom surface 1B of the neutron moderator 1. The second intermediate layered body 21, the first intermediate layered body 11, and the third intermediate layered body 31 are layered to form the neutron moderator 1 illustrated in FIG. 2 to FIG. 5.

In other words, the neutron moderator 1 is configured such that the first sintered compacts ds1, the disc-shaped second sintered compacts ds2 without a through hole H1, and the disc-shaped third sintered compacts ds3 without a through hole H1 are combined and layered. With this configuration, a machined body made of magnesium fluoride can be readily prepared. Accordingly, the neutron moderator 1 can be manufactured easily.

The first sintered compacts ds1, the second sintered compacts ds2, and the third sintered compacts ds3 are obtained by applying mechanical pressure and a direct current with the waveform of an ON-OFF pulse voltage to sinter the magnesium fluoride powder material M (pulsed electric current sintering). The pulsed electric current sintering increases the relative density of the magnesium fluoride powder material M. The first sintered compacts ds1, the second sintered compacts ds2, and the third sintered compacts ds3 are thus formed as magnesium fluoride sintered compacts having less variation in grain size and suppressed grain growth, thereby preventing cracking or chipping.

The magnesium fluoride powder material M filled at the first powder filling process S11, the second powder filling process S21, and the third powder filling process S31 is a high-purity material having a purity of 99 percent by mass or higher and the balance may contain inevitable impurities. This configuration gives satisfactory performance for moderating neutrons per unit volume of the sintered compact and is advantageous in that the sintered compact per se need not be designed to have a large size even when the relative density after sintering is reduced to some extent. The neutron moderator 1 can suppress neutrons having energy of lower than 0.5 eV. The magnesium fluoride sintered compact ds can also suppress neutrons having energy of higher than 10 keV.

The method for manufacturing the first sintered compact includes: the first powder filling process S11 of filling the magnesium fluoride powder material M by tapping in the sintering die having the core CR at the center position in a planer view; and the first sintered compact sintering process S12 of applying mechanical pressure and a direct current with the waveform of an ON-OFF pulse voltage to the magnesium fluoride powder material M filled at the first powder filling process S11 to sinter the magnesium fluoride powder material M (pulsed electric current sintering), to obtain the magnesium fluoride sintered compact having the through hole H1 at the center. The coefficient of thermal expansion of the core CR is equivalent to that of the magnesium fluoride sintered compact. In this method, the first sintered compact ds1 is sintered by the near net shape technique with a reduced number of machining processes, thereby suppressing cracking or chipping.

In the method for manufacturing the first sintered compact, the magnesium fluoride sintered compact having the through hole H1 at the center is machined at the first sintered compact machining process S15, and after the first sintered compact machining process S15, the first intermediate layered body 11 is obtained as a magnesium fluoride machined body having the tapered surface 1C. The magnesium fluoride machined body having the tapered surface 1C may be a single layer of the first sintered compact ds1. The method for manufacturing the neutron moderator 1 includes the process of layering and joining the magnesium fluoride bodies each having the tapered surface 1C (in the embodiment, the first intermediate layered body 11) and the second sintered compacts ds2 in the form of the disc-shaped magnesium fluoride sintered compacts in combination. This method eliminates the need for sintering a magnesium fluoride sintered compact having a large thickness, thereby lowering the possibility that the relative density is reduced in the neutron moderator 1. This manufacturing method allows the magnesium fluoride sintered compacts having poor workability to be thin, thereby improving the precision in machining the through holes H1 passing through each first sintered compact ds1 to have the tapered surface 1C.

The neutron moderator 1 includes the disc-shaped sintered compacts ds3 in which the tapering is performed on their outer peripheries by machining at S34. The third sintered compacts ds3 are made thin, which improves the precision in machining the magnesium fluoride sintered compacts ds that are prone to cracking or chipping.

The neutron moderator 1 is a magnesium fluoride sintered compact free from cracks or chips and having a high relative density, and thus can suppress neutrons having energy of lower than 0.5 eV. The neutron moderator 1 is a magnesium fluoride sintered compact free from cracks or chips and having a high relative density, and thus can suppress neutrons having energy of higher than 10 keV.

The neutron moderator 1 includes the first intermediate layered body 11, the second intermediate layered body 21, and the third intermediate layered body 31, which are in a layered state, and thus exhibits uniform performance for moderating neutrons at any layered body.

Modification of First Sintered Compact

Figure 21:
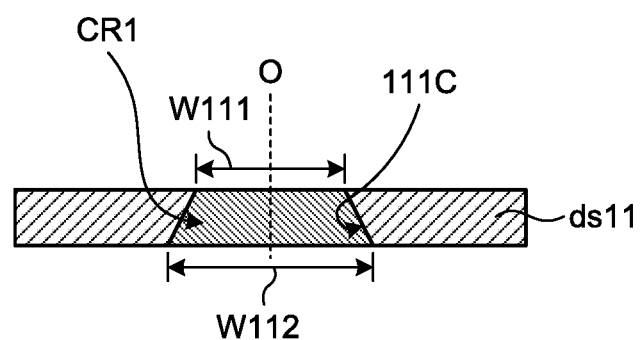
FIG. 21 is a side view of a first ring of the first sintered compact according to a modification of the embodiment.
Figure 22:
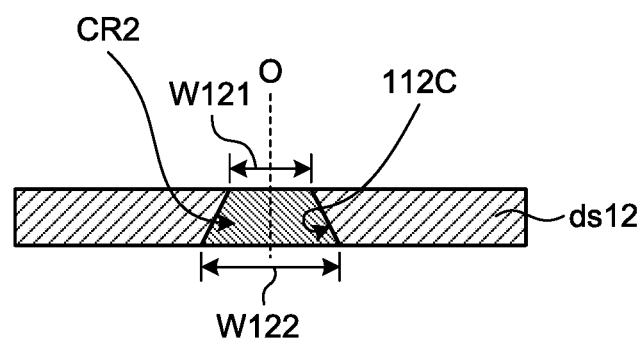
FIG. 22 is a side view of a second ring of the first sintered compact according to the modification of the embodiment.
Figure 23:
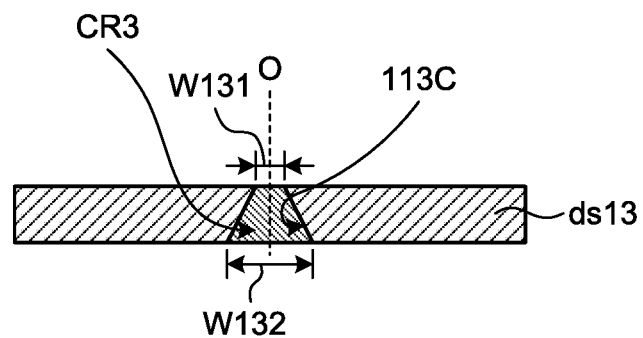
FIG. 23 is a side view of a third ring of the first sintered compact according to the modification of the embodiment.

FIG. 21 is a side view of a first ring of the first sintered compact according to a modification of the embodiment. FIG. 22 is a side view of a second ring of the first sintered compact according to the modification of the embodiment. FIG. 23 is a side view of a third ring of the first sintered compact according to the modification of the embodiment. In the modification of the embodiment, the core disposed at the center position of the sintering die in FIG. 7 in a planer view is changed from a cylindrical shape into a truncated cone shape.

A core CR1 illustrated in FIG. 21 has a truncated cone shape, a top surface of which is a circular cross section with a diameter W111, and a bottom surface of which is a circular cross section with a diameter W112. As a result, a sintered first ring ds11 of the first sintered compact has a through hole having a tapered surface 111C at the position of the center axis O.

A core CR2 illustrated in FIG. 22 has a truncated cone shape, a top surface of which is a circular cross section with a diameter W121, and a bottom surface of which is a circular cross section with a diameter W122. As a result, a sintered second ring ds12 of the first sintered compact has a through hole having a tapered surface 112C at the position of the center axis O.

A core CR3 illustrated in FIG. 23 has a truncated cone shape, a top surface of which is a circular cross section with a diameter W131, and a bottom surface of which is a circular cross section with a diameter W132. As a result, a sintered third ring ds13 of the first sintered compact has a through hole having a tapered surface 113C at the position of the center axis O.

Figure 24:
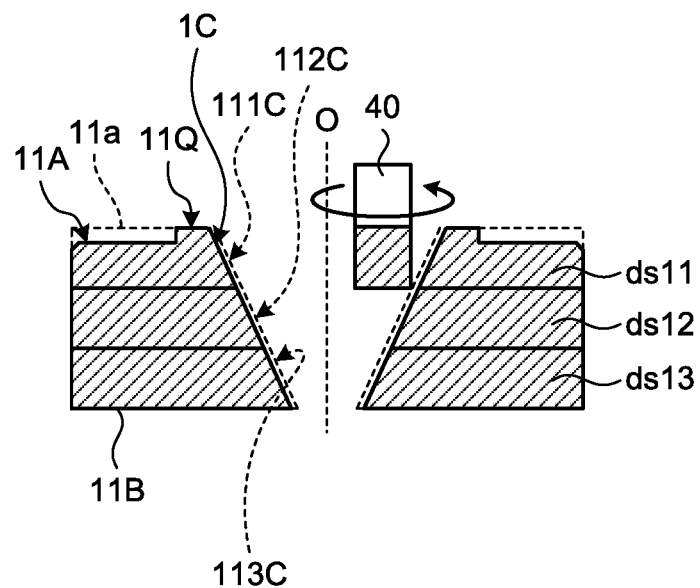
FIG. 24 is a diagram for explaining a machining process for manufacturing a first intermediate layered body according to the modification of the embodiment.

FIG. 24 is a diagram for explaining a machining process for manufacturing a first intermediate layered body according to the modification of the embodiment. A first intermediate layered body 11 according to the modification of the embodiment is, as illustrated in FIG. 24, formed by layering the first ring ds11, the second ring ds12, and the third ring ds13. As illustrated in FIG. 24, at the first sintered compact machining process S15 according to the modification of the embodiment, the drill 40 which spirally revolves while rotating around its own axis is inserted into the through holes of the first ring ds11, the second ring ds12, and the third ring ds13 stacked on each other, to bore the tapered surface 111C in FIG. 21, the tapered surface 112C in FIG. 22, and the tapered surface 113C in FIG. 23 to form the tapered surface 1C illustrated in FIG. 24. As illustrated in FIG. 24, since the through holes have tapered surfaces in advance, the amount of machining can be reduced.

Modification of Third Sintered Compact

Figure 25:
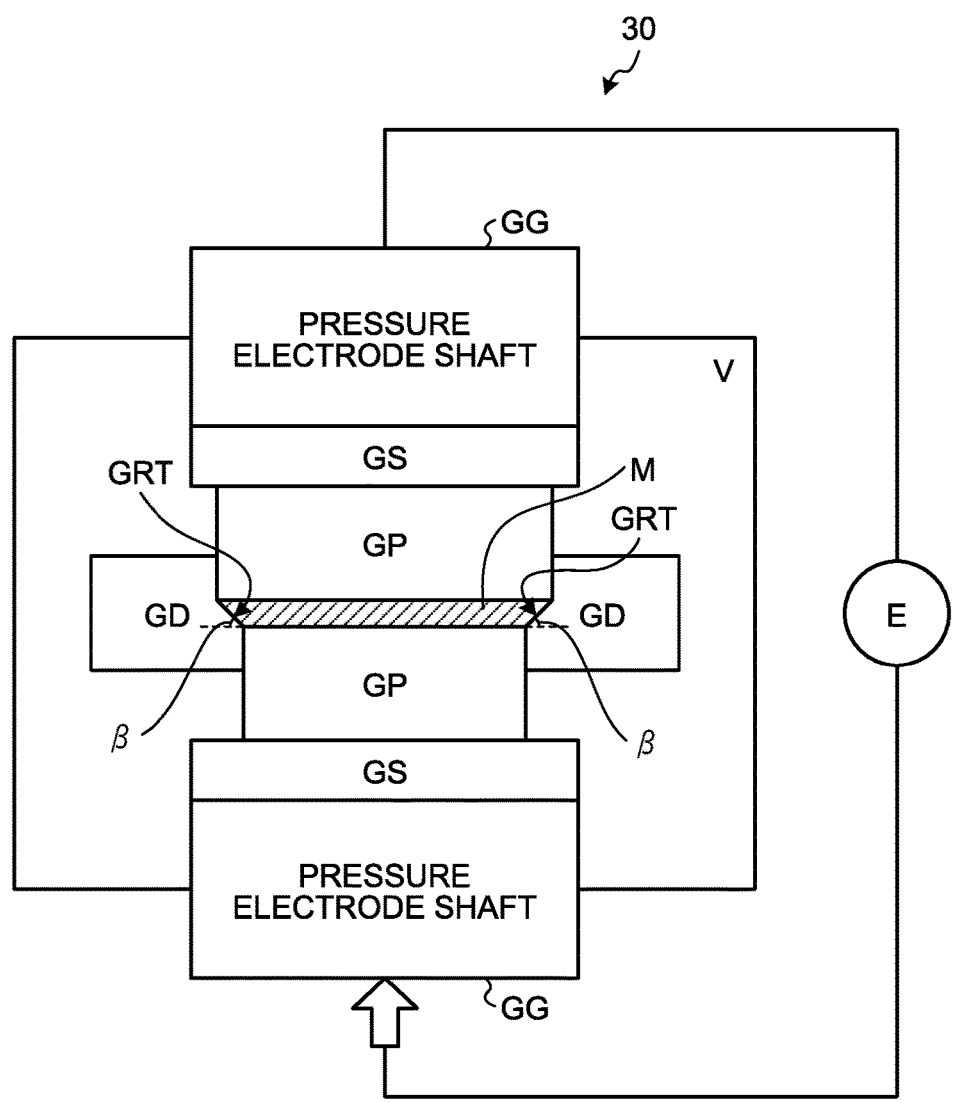
FIG. 25 is a diagram schematically illustrating a pulsed electric current sintering device for manufacturing a modification of the third sintered compact.

FIG. 25 is a diagram schematically illustrating a pulsed electric current sintering device for manufacturing the modification of the third sintered compact. The third sintered compact ds3 is a disc-shaped magnesium fluoride sintered compact having a tapered outer peripheral surface. As described above, the outer periphery of the disc-shaped magnesium fluoride sintered compact has the tapered surface 1T with the diameter gradually changing along the center axis. In the modification of the third sintered compact, the tapered surface 1T is formed with a frame die GD of a sintering die. The frame die GD is a ring-shaped frame die positioned on the outer periphery of the sintering die and has a tapered surface GRT with an inner diameter at an angle β. The third sintered compact ds3 after sintering thus has a tapered outer peripheral surface, which prevents cracking or chipping. The neutron moderator 1 includes at least one disc-shaped third sintered compact ds3, the outer peripheral surface of which is tapered after sintering and that has no through hole H1. Using the frame die GD having a tapered surface allows the third sintered compact ds3 having a tapered outer peripheral surface to be directly produced as illustrated in FIG. 18, thereby reducing the number of manufacturing processes.

EXAMPLES

To obtain samples, a magnesium fluoride powder (manufactured by Morita Chemical Industries Co., Ltd.) having a purity of 99% or higher was filled in a sintering die having an interior volume of diameter $\phi$ (mm)×thickness (mm), and powder filling was performed by tapping. A cylindrical core was disposed at the center of the sintering die.

Figure 26:
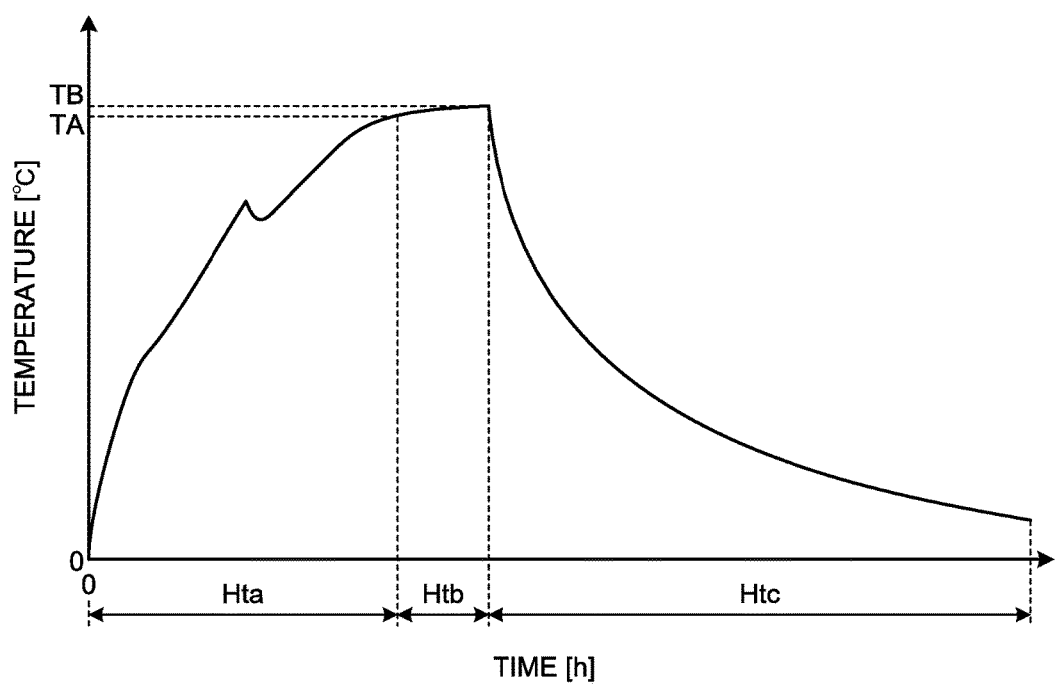
FIG. 26 is a graph illustrating the heating state of pulsed electric current sintering.

Subsequently, a vessel filled with magnesium fluoride powder was set in a pulsed electric current sintering device. In the pulsed electric current sintering device, a vacuum atmosphere was created as a sintering atmosphere by decompression. Magnesium fluoride sintered compacts were manufactured under the same pressure condition of 10 MPa to 20 MPa in the pulsed electric current sintering device for all the samples. The samples of example 1 to example 4 and comparative example 1 and comparative example 2 were magnesium fluoride sintered compacts obtained by sintering magnesium fluoride powder while a direct current with the waveform of an ON-OFF pulse voltage was applied thereto. The electric current conditions of the pulsed electric current sintering device were the same in the examples and the comparative examples. For the samples in example 1 to example 4 and comparative example 1 and comparative example 2, a direct current with the waveform of an ON-OFF pulse voltage was applied for sintering such that the maximum current output was about 18000 A. FIG. 26 is a graph illustrating a heating state of pulsed electric current sintering. The magnesium fluoride powder of the samples was heated at a heating rate adjusted in a range from 1° C./min to 15° C./min until it reached the heating maximum point TA at the heating time Hta illustrated in FIG. 26, and the holding temperature TB illustrated in FIG. 26 was held for the holding time Htb. Heating was performed at holding temperatures in a range from 750° C. to 770° C. The holding time was set in a range from 150 minutes to 180 minutes. After the elapse of the holding time Htb, the samples were cooled for the slow cooling time Htc until they reached the room temperature. After cracking was checked, samples free from cracks were denoted by example 1 to example 4, and samples with cracks were denoted by comparative example 1 and comparative example 2.

TABLE 1

| | Sintered compact density (%) | Heating time (min) | Heating maximum point (° C.) | Holding time (min) | Holding temperature (° C.) | Thickness before sintering (mm) | Thickness after sintering (mm) | Core material | Sintering cracking | Machining cracking | Total evaluation |
|---|---|---|---|---|---|---|---|---|---|---|---|
| Example 1 | 95.6 | 720 | 750 | 150 | 750 | 35.0 | 37.07 | NiFeCr alloy | Not found | Not found | Good |
| Example 2 | 95.9 | 720 | 750 | 150 | 750 | 35.0 | 37.01 | NiFeCr alloy | Not found | Not found | Good |

TABLE 1-continued

| | Sintered compact density (%) | Heating time (min) | Heating maximum point (° C.) | Holding time (min) | Holding temperature (° C.) | Thickness before sintering (mm) | Thickness after sintering (mm) | Core material | Sintering cracking | Machining cracking | Total evaluation |
|---|---|---|---|---|---|---|---|---|---|---|---|
| Example 3 | 95.9 | 720 | 750 | 180 | 750 | 35.0 | 36.96 | NiFeCr alloy | Not found | Not found | Good |
| Example 4 | 95.9 | 720 | 750 | 180 | 750 | 35.0 | 36.93 | NiFeCr alloy | Not found | Not found | Good |
| Comparative example 1 | 94.6 | 750 | 750 | 150 | 760 | 35.0 | 37.42 | NiFeCr alloy | Not found | Found | Poor |
| Comparative example 2 | 96.5 | 690 | 760 | 150 | 760 | 35.0 | 36.67 | Graphite | Found | — | Poor |

According to the findings from the examples, when the core is made of an NiFeCr alloy, sintering cracks did not occur after the sintering process as in example 1 to example 4 and comparative example 1 (denoted as "not found" in Table 1). By contrast, when the core is made of graphite, sintering cracks occurred after the sintering process (denoted as "found" in Table 1).

Graphite has a melting point of 3500° C. and seems suitable for cores. However, the coefficient of thermal expansion of graphite is $5.6 \times 10^{-6}/°$ C. to $7.1 \times 10^{-6}/°$ C. This coefficient of thermal expansion of graphite does not fall within the range of the coefficient of thermal expansion of magnesium fluoride from $8.48 \times 10^{-6}/°$ C. to $13.7 \times 10^{-6}/°$ C. Sintering cracks after the sintering process are thought to occur since the coefficient of thermal expansion of graphite is not equivalent to that of magnesium fluoride. By contrast, when the core is made of an NiFeCr alloy, the coefficient of thermal expansion of the core is equivalent to that of magnesium fluoride, and sintering cracks after the sintering process are suppressed.

According to the findings from the examples, in example 1 to example 4 and. comparative example 1 of the magnesium fluoride sintered compacts each having a through hole at the center, the drill 40 which spirally revolved while rotating around its own axis was inserted into the through hole H1 to bore the tapered surface 1C illustrated in FIG. 11. In example 1 to example 4, machining cracks did not occur (denoted as "not found" in Table 1). By contrast, in comparative example 1, sintering cracks after the machining process occurred (denoted as "found" in Table 1).

According to the findings from the examples, the relative density in each of example 1 to example 4 and comparative example 1 was measured, and the relative density in each of example 1 to example 4 was 95% or higher, whereas the relative density of comparative example 1 was smaller than 95%. This reveals that machining cracks can be suppressed if sintering is performed such that the relative density of the magnesium fluoride sintered compact is 95% or higher.

According to the findings from the examples, the magnesium fluoride powder is not limited to a specific powder as long as it has high purity and a concentration of 99.0% or higher. General magnesium fluoride powder may be used, such as powder obtained by adding hydrofluoric acid to a cation exchange resin, the cation exchange group of which is generally magnesium, and then extracting and powdering the produced magnesium fluoride particles, for example.

According to the findings from the examples, the pressurizing condition for the method for manufacturing the magnesium fluoride sintered compact is preferably about 20 MPa. If the pressurizing condition is lower than 20 MPa, the magnesium fluoride powder material M is not sufficiently compressed and large gaps are left among powder particles, which may cause cracking in the magnesium fluoride sintered compact. If the pressurizing condition is higher than 20 MPa, the outer periphery of the magnesium fluoride sintered compact may be prone to damage. If the pressurizing condition is higher than 20 MPa, there is a problem in terms of the specification of a manufacturing device, that is, a performance problem of the manufacturing device that has a difficulty in applying high pressure to a large-sized magnesium fluoride sintered compact. Sintering is preferably performed under the constant pressurizing condition, under which the crystalline structure of a sintered compact tends to become uniform.

According to the findings from the examples, the holding temperature in the method for manufacturing the magnesium fluoride sintered compact is preferably from 650 to 800° C. The holding temperature of lower than 650° C. requires longer holding time to obtain uniform crystal grains, while the holding temperature of higher than 800° C. is not cost-effective, because the effect is saturated.

According to the findings from the examples, in the method for manufacturing the magnesium fluoride sintered compact, the holding time for heating the sintering die after sintering and holding the temperature is preferably 45 minutes or longer. The holding time of longer than 180 minutes may increase manufacturing cost, because the effect is saturated.

What is claimed is:

1. A magnesium fluoride sintered compact comprising:
   a disc-shaped magnesium fluoride sintered compact having a through hole passing through a center axis of the disc-shaped magnesium fluoride sintered compact, wherein the magnesium fluoride sintered compact has a relative density of 95% or higher.

2. The magnesium fluoride sintered compact according to claim 1, wherein the through hole has a tapered inner wall with a diameter gradually changing along the center axis.

3. A neutron moderator comprising:
   a plurality of the magnesium fluoride sintered compacts according to claim 2; and
   a plurality of disc-shaped magnesium fluoride sintered compacts without a through hole, wherein
   the magnesium fluoride sintered compacts and the magnesium fluoride sintered compacts without a through hole are combined and layered.

4. A neutron moderator comprising:
   a plurality of the magnesium fluoride sintered compacts according to claim 1; and
   a plurality of disc-shaped magnesium fluoride sintered compacts without a through hole, wherein
   the magnesium fluoride sintered compacts and the magnesium fluoride sintered compacts without a through hole are combined and layered.

5. The neutron moderator according to claim 4, wherein at least one of the disc-shaped magnesium fluoride sintered compacts without a through hole has a tapered outer peripheral surface.

6. A method for manufacturing a magnesium fluoride sintered compact, the method comprising:
　　filling a magnesium fluoride powder material into a sintering die by tapping, the sintering die being provided with a core at a center position in a planar view; and
　　performing pulsed electric current sintering for sintering the filled magnesium fluoride powder material while applying mechanical pressure and a direct current with a waveform of an ON-OFF pulse voltage thereto, to obtain a magnesium fluoride sintered compact having a through hole at a center thereof, wherein the core has a coefficient of thermal expansion equivalent to a coefficient of thermal expansion of the magnesium fluoride sintered compact.

7. The method for manufacturing a magnesium fluoride sintered compact according to claim 6, wherein the core is made of a nickel-based alloy.

8. The method for manufacturing a magnesium fluoride sintered compact according to claim 7, wherein in the powder filling, the magnesium fluoride powder material is a high-purity material having a purity of 99 percent by mass or higher, the balance being inevitable impurities.

9. The method for manufacturing a magnesium fluoride sintered compact according to claim 6, wherein in the powder filling, the magnesium fluoride powder material is a high-purity material having a purity of 99 percent by mass or higher, the balance being inevitable impurities.

10. A method for manufacturing a neutron moderator, the method comprising:
　　preparing a plurality of magnesium fluoride sintered compacts, each having the through hole at the center and being manufactured by the method for manufacturing a magnesium fluoride sintered compact according to claim 6;
　　machining the magnesium fluoride sintered compacts each having the through hole at the center; and
　　layering and joining together the magnesium fluoride machined bodies each having the through hole after the machining and a plurality of disc-shaped magnesium fluoride sintered compacts in combination.

11. The method for manufacturing a neutron moderator according to claim 10, wherein the machining includes tapering the through hole at the center for the magnesium fluoride sintered compacts each having the through hole at the center.

12. The method for manufacturing a neutron moderator according to claim 11, wherein the disc-shaped magnesium fluoride sintered compacts each have a tapered outer peripheral shape.

13. The method for manufacturing a neutron moderator according to claim 11, wherein sintered molded bodies each having a tapered outer peripheral shape are obtained as the disc-shaped magnesium fluoride sintered compacts.

14. The method for manufacturing a neutron moderator according to claim 10, wherein the disc-shaped magnesium fluoride sintered compacts each have a tapered outer peripheral shape.

15. The method for manufacturing a neutron moderator according to claim 10, wherein sintered molded bodies each having a tapered outer peripheral shape are obtained as the disc-shaped magnesium fluoride sintered compacts.

* * * * *